United States Patent
O'Neil et al.

(10) Patent No.: US 10,405,987 B2
(45) Date of Patent: Sep. 10, 2019

(54) PATIENT-SPECIFIC SPINAL FUSION CAGE AND METHODS OF MAKING SAME

(71) Applicant: DePuy Synthes Products, Inc., Raynham, MA (US)

(72) Inventors: Michael J O'Neil, West Barnstable, MA (US); Roman Lomeli, Plymouth, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/668,458

(22) Filed: Aug. 3, 2017

(65) Prior Publication Data

US 2017/0354510 A1 Dec. 14, 2017

Related U.S. Application Data

(63) Continuation of application No. 14/260,771, filed on Apr. 24, 2014, now Pat. No. 9,757,245.

(51) Int. Cl.
*A61F 2/44* (2006.01)
*A61B 8/12* (2006.01)
(Continued)

(52) U.S. Cl.
CPC ............ *A61F 2/442* (2013.01); *A61B 5/0084* (2013.01); *A61B 5/45* (2013.01); *A61B 8/12* (2013.01); *A61F 2/30942* (2013.01); *A61F 2/4455* (2013.01); *A61F 2/4684* (2013.01); *A61F 2002/30387* (2013.01); *A61F 2002/30556* (2013.01); *A61F 2002/30579* (2013.01); *A61F 2002/30581* (2013.01); *A61F 2002/30604* (2013.01); *A61F 2002/30971* (2013.01); *A61F 2002/30985* (2013.01);
(Continued)

(58) Field of Classification Search
CPC .......... A61F 2/46; A61F 2/4455–2/447; A61F 2/4611; A61F 2/4684; A61F 2/44; A61F 2/4657
See application file for complete search history.

(56) References Cited

U.S. PATENT DOCUMENTS

| 4,575,805 A | 3/1986 | Moermann |
| 5,514,180 A | 5/1996 | Heggeness |

(Continued)

OTHER PUBLICATIONS

Marchi et al., "Radiographic and clinical evaluation of cage subsidence after stand-alone lateral interbody fusion", J Neurosurg Soine 19, pp. 110-118, 2013.
(Continued)

*Primary Examiner* — Lynnsy M Summitt

(57) ABSTRACT

A method of determining disc space geometry with the use of an expandable trial having endplate-mapping capabilities. An expandable trial is inserted into the disc space and its height is adjusted to obtain the desired decompression and spinal alignment (which is typically confirmed with the use of CT or Fluoroscopic imaging). The endplate dome/geometry dome is then determined by one of the following three methods:
  a) direct imaging through the trial,
  b) balloon moldings filled with flowable in-situ fluid (for example, silicon, polyurethane, or PMMA) from superior/inferior endplates or
  c) light-based imaging through superior & inferior balloons.

6 Claims, 6 Drawing Sheets

(51) Int. Cl.
*A61F 2/30* (2006.01)
*A61F 2/46* (2006.01)
*A61B 5/00* (2006.01)

(52) U.S. Cl.
CPC . *A61F 2002/469* (2013.01); *A61F 2002/4663* (2013.01); *A61F 2002/4689* (2013.01); *A61F 2002/4696* (2013.01)

(56) References Cited

U.S. PATENT DOCUMENTS

| | | | |
|---|---|---|---|
| 6,425,920 | B1 | 7/2002 | Hamada |
| 6,932,842 | B1 | 8/2005 | Litschko |
| 8,116,853 | B2 | 2/2012 | Hart |
| 8,246,680 | B2 | 8/2012 | Betz |
| 8,384,916 | B2 | 2/2013 | Hart |
| 8,394,142 | B2 | 3/2013 | Bertagnoli |
| 8,619,154 | B2 | 12/2013 | Hart |
| 8,870,889 | B2 | 10/2014 | Frey |
| 9,198,678 | B2 | 12/2015 | Frey |
| 2002/0007294 | A1 | 1/2002 | Bradbury |
| 2004/0236342 | A1 | 11/2004 | Ferree |
| 2004/0236424 | A1* | 11/2004 | Berez ............... A61B 5/1076 623/14.12 |
| 2005/0043835 | A1 | 2/2005 | Christensen |
| 2005/0273172 | A1 | 12/2005 | Patil |
| 2006/0069436 | A1* | 3/2006 | Sutton ............... A61B 5/0538 623/17.13 |
| 2007/0118243 | A1 | 5/2007 | Schroeder |
| 2007/0162136 | A1 | 7/2007 | O'Neil |
| 2008/0161680 | A1 | 7/2008 | von Jako |
| 2009/0112221 | A1* | 4/2009 | Burke ............... A61F 2/4657 606/102 |
| 2010/0086181 | A1 | 4/2010 | Zug |
| 2010/0292963 | A1 | 11/2010 | Schroeder |
| 2011/0144752 | A1 | 6/2011 | Defelice |
| 2011/0257655 | A1* | 10/2011 | Copf, Jr. ............... A61B 17/025 606/90 |
| 2012/0323247 | A1 | 12/2012 | Bettenga |
| 2013/0002426 | A1 | 1/2013 | Hart |
| 2013/0204157 | A1 | 8/2013 | Clark |
| 2014/0002613 | A1 | 1/2014 | Hart |
| 2014/0031676 | A1 | 1/2014 | Nempont |
| 2014/0074441 | A1 | 3/2014 | Fitz |
| 2016/0030067 | A1 | 2/2016 | Frey |

OTHER PUBLICATIONS de Beer et.al., "Reducing subsidence risk by using rapid manufactured patient-specific intervertebral disc implants", SQine Journal 12, pp. 1060-1066, 2012.

* cited by examiner

PATIENT-SPECIFIC SPINAL FUSION CAGE AND METHODS OF MAKING SAME

CONTINUING DATA

This application claims priority from co-pending U.S. Ser. No. 14/260,771, filed Apr. 24, 2014, entitled "Patient-Specific Spinal Fusion Cage and Methods of Making Same" (O'Neil), the specification of which is incorporated by reference in its entirety.

BACKGROUND OF THE INVENTION

Spinal fusion cage subsidence and expulsion are frequently issues of concern in spinal fusion surgeries. Restenosis due to subsidence has been often documented. See, for example, Marchi et al., *J Neurosurg Spine* 19, 110-118, 2013. Four subsidence grades have been developed and shown to correlate with the likelihood of restenosis and associated revision rates. The significant potential of endplate-conforming implants in reducing the likelihood of subsidence has also been considered. See, for example, de Beer et. al., *Spine Journal* 12, 1060-1066, 2012.

Insufficient contact area and load transfer between the vertebral body and the cage can produce excessive load transfer in specific locations that can lead the cage to settle or subside into the vertebral body. Insufficient contact area or pressure differentials between the cage and the vertebral bodies can also produce micro-motions and/or macro-motions that can increase subsidence and result in cage expulsion from the disc space. It is believed that this insufficient contact area is in part due to the anatomical variability in the curvature of the endplates from level to level and patient to patient. Additionally, low bone mineral density index or overaggressive decortications of the endplate can reduce the strength of the endplate and the ability to transfer load from vertebral body to vertebral body.

To minimize these risks, surgeons carefully prepare the opposing vertebral endplates and typically insert the cage having as large a footprint as possible in order to maximize the contact area. When appropriate, the surgeon also places the cage on the apophyseal rings to provide as much support and load transfer as possible for spinal distraction while ensuring the cage is securely nested within the disc space.

These concerns have also been addressed by modifying the shape of the intervertebral cage. Although some cages have been domed to increase contact area, these are often unable to fit and conform to each disc space due to inherent human anatomical variability.

Other procedures concern the use of preoperative CT- or MRI-derived data to facilitate the manufacturing of patient-specific spinal devices. A significant limitation with these devices and patents is that they assume the correct disc space geometry can be clearly identified prior to surgical intervention for disc space released, FSU decompression and spinal alignment corrections. Additionally, the state of the art does not include patient-specific intra-operatively fabricated cages nor patient-specific intra-operatively assembled cages.

U.S. Pat. No. 5,514,180 (Heggeness) discloses intervertebral devices having fixed shapes for accommodating the defined surface contours of vertebral endplates. A method for quantitatively determining the three-dimensional morphology of vertebral surfaces, particularly vertebral endplates, is also disclosed.

SUMMARY OF THE INVENTION

The present invention relates to the intra-operative determination of a desired cage footprint, height, lordosis, 3D geometry and endplate contact area, once spinal disc space intervention and decompression have been achieved and spinal alignment has been determined. The present invention provides certain patient-specific spinal fusion cages as well as the method of determination, fabrication and implantation of these patient-specific spinal fusion devices. This method and devices allow for the intra-operative determination, fabrication and implantation of custom, patient-specific implants to maximize contact area between the prepared endplates and the fusion cage with the objective of reducing subsidence and expulsion.

In one embodiment of the present invention, there is provided a method of determining disc space geometry with the use of an expandable trial having endplate-mapping capabilities. In one preferred embodiment, an expandable trial is inserted into the disc space and its height is then adjusted to obtain the desired decompression and spinal alignment (which is typically confirmed with the use of CT- or fluoroscopic imaging). The geometry of the dome (i.e., the cavity between the trial and the endplates) is then determined by one of the following three methods:
  a) direct light or ultrasound imaging through the trial,
  b) balloon moldings filled with a flowable, in-situ fluid (for example, thermosets such as silicone, polyurethane, or an acrylic polymer such as PMMA, or thermoplastics) attached to superior/inferior prosthetic endplates or
  c) light absorption imaging through superior & inferior balloons attached to superior/inferior prosthetic endplates.

Therefore, in accordance with the present invention, there is provided an intervertebral trial having a distal end portion having upper and lower surfaces defining a height therebetween, wherein the height is adjustable and is adapted for insertion into a disc space between opposing vertebral endplates, and wherein the distal end portion has a functional feature adapted to map a contour of a vertebral endplate.

Also in accordance with the present invention, there is provided a method of imaging an contour of a vertebral endplate, comprising the steps of;
  a) selecting the trial described above,
  b) inserting the trial into the disc space,
  c) expanding the height of the trial to create a first cavity between the upper surface of the trial and the upper vertebral endplate, and
  d) producing an electronic 3D image of the first cavity.

Also in accordance with the present invention, there is provided a method of manufacturing a patient-specific intravertebral implant for a patient having a disc space defined by a pair of opposed vertebral endplates, comprising the steps of:
  a) intraoperatively obtaining a 3D image of each of the vertebral endplates,
  b) intraoperatively manufacturing, from the 3D images, the patient-specific intervertebral implant, and
  c) inserting the patient-specific intervertebral implant into the disc space in the patient.

Also in accordance with the present invention, there is provided a method of building a patient specific intravertebral implant for a patient having a disc space defined by a pair of opposed vertebral endplates, comprising the steps of:
  a) intraoperatively obtaining a 3D image of each of the endplates,
  b) intraoperatively manufacturing, from the 3D images, a pair of prosthetic endplates, c) intraoperatively attaching each prosthetic endplate to a core component to produce an assembled, patient specific intravertebral implant.

d) inserting the assembled patient specific intravertebral implant into a disc space in the patient.

Also in accordance with the present invention, there is provided a patient-specific intervertebral fusion cage for insertion into a disc space defined by opposing upper and lower vertebral endplates in a patient, comprising:

a) an intermediate modular core component having an upper surface and a lower surface, b) an upper endplate attached to the upper surface of the core component, c) a lower endplate attached to the lower surface of the core component, wherein each of the upper and lower endplates are manufactured from 3D images of the opposing upper and lower vertebral endplates of the patient.

DETAILED DESCRIPTION OF THE INVENTION

Figure 1A:
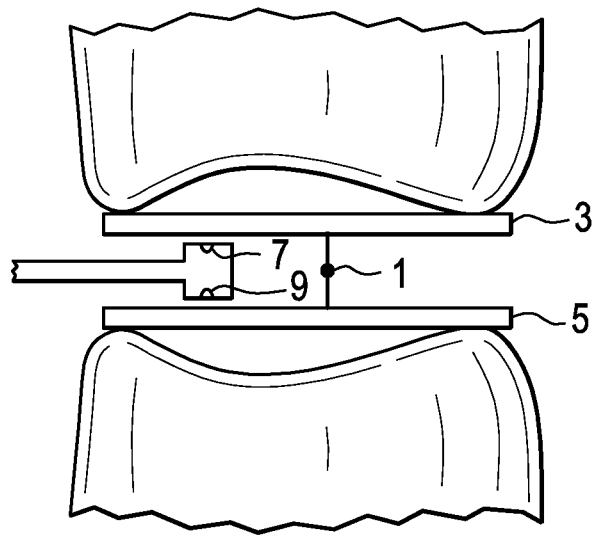
FIGS. 1A-1B disclose front and side views of a direct imaging embodiment of the present invention.

In general, the trial of the present invention comprises the aforesaid distal portion, a proximal end portion comprising a handle, and an elongated intermediate portion. Preferably, the elongated intermediate portion comprises a rod. Also preferably, the upper and lower surfaces are substantially planar.

In one embodiment of the invention, the imaging feature comprises an endoscope having a light emitter, such as a fiber optic. In this embodiment, the light emitter emits light waves into the cavity between the trial and the vertebral endplate to create return signals. A monitoring system including a camera creates a 3D image of the cavity from the return signals. A screen may also provide a visual identification of the endplate contour.

In one embodiment, the fiber optic emits light waves from a tip of a fiber optic into the cavity between the vertebral endplate and the trial. Light waves are emitted at frequencies sufficient to image endplate contours. In this embodiment, the fiber optic emits light waves in a direction normal to the upper or lower surface of the trial. Light waves are continuously emitted and contact a vertebral endplate as the camera traverses the upper surface of the trial. In alternative embodiments, fiber optic emits light waves intermittently. The light waves return, and the signals from the returning light waves are collected by the camera and transmitted to a signal receiver. The monitoring system uses the signals received by the signal receiver to create a 3D image of the vertebral endplate contour. The signal receiver includes any device suitable for receiving a light signal. The signal receiver may be located at any suitable location. In one embodiment, the signal receiver is located in proximity to the patient upon which the endoscope is being used. For instance, in an embodiment, the signal receiver is located in the operating room with the patient. The monitoring system comprises any devices and methods suitable for providing a 3D image from signals created by light waves contacting internal body structures. In an embodiment, the monitoring system comprises a camera. The camera includes any device suitable for photography, wherein photography refers to diagnostic imaging in which light is used to image internal body structures. The monitoring system may be located at any suitable location. In an embodiment, the monitoring system is located in proximity to the patient upon which the endoscope is being used. For instance, in an embodiment, the monitoring system is located in the operating room with the patient. The monitoring system may also include a light imaging screen. The light imaging screen includes any screen suitable for displaying the image of internal body structures such as the vertebral endplate. In an embodiment, the monitoring system comprises the signal receiver.

In one embodiment, the monitoring system allows for the distance from light emitter to the vertebral endplate to be determined, visualized on a viewing screen, and aggregated into a 3D image of the cavity. The distance may be determined by any suitable distance determination techniques used with monitoring systems.

In one embodiment, the camera is a wireless camera. A wireless camera may be powered by any suitable power source such as battery power, magnetic induction resonance, and the like. Any magnetic induction resonance method suitable for use with a surgical camera may be used. In one embodiment, the camera is powered through magnetic induction resonance between an ex vivo source and a receiver. In one embodiment, the receiver is contained within or alternatively on the camera.

In one embodiment, this 3D image created from light signals is then used to create a patient-specific intervertebral implant. In one embodiment thereof, this 3D image is then used to create a patient-specific endplate that can be attached to a modular core component of an intervertebral implant.

In one embodiment of the invention, the imaging feature comprises an ultrasound emitter, or transducer. In this embodiment, the ultrasound transducer emits sound waves into the cavity between the trial and the vertebral endplate to create return signals. The monitoring system includes an ultrasound imaging device that creates a 3D image of the cavity from the return signals. An ultrasound imaging screen may also provide a visual identification of the endplate contour.

In one embodiment, the ultrasound transducer emits sound waves from a tip into the cavity between the endplate and the trial. Sound waves are emitted at frequencies sufficient to image endplate contours. In one embodiment, the transducer emits sound waves in a direction normal to the upper surface of the trial. In some embodiments, sound waves are continuously emitted and contact a vertebral endplate as the transducer traverses the upper or lower surface of the trial. In alternative embodiments, transducer emits sounds waves intermittently. The sound waves return, and the signals from the returning sound waves are collected by the transducer and transmitted to a signal receiver. A monitoring system uses the signals received by the signal receiver to create a 3D image of the cavity between the vertebral endplate and the trial. The signal receiver includes any device suitable for receiving a signal from an ultrasound transducer. The signal receiver may be located at any suitable location. In an embodiment, the signal receiver is located in proximity to the patient upon which ultrasound transducer is being used. For instance, in an embodiment, the signal receiver is located in the operating room with the patient. The monitoring system comprises any devices and methods suitable for providing a 3D image from signals created by sound waves contacting internal body structures. In an embodiment, the monitoring system comprises an ultrasound device. The ultrasound device includes any device suitable for ultrasonography. It is to be understood that ultrasonography refers to diagnostic imaging in which ultrasound is used to image internal body structures. The monitoring system may be located at any suitable location. In an embodiment, the monitoring system is located in proximity to the patient upon which the transducer is being used. For instance, in an embodiment, the monitoring system is located in the operating room with the patient. The monitoring system may also include an ultrasound imaging screen. Ultrasound imaging screen includes any screen suitable for displaying the image of internal body structures such as the vertebral endplate. In an embodiment, the monitoring system comprises the signal receiver.

In one embodiment, the monitoring system allows for the distance from ultrasound transducer to the vertebral endplate to be determined, visualized on ultrasound imaging screen, and aggregated into a 3D image of the cavity. The distance may be determined by any suitable distance determination techniques used with monitoring systems such as ultrasound devices.

In one embodiment, the transducer is a wireless transducer. A wireless transducer may be powered by any suitable power source such as battery power, magnetic induction resonance, and the like. In one embodiment, ultrasound transducer is powered through magnetic induction resonance between an ex vivo source and a receiver. In one embodiment, the receiver is contained within or alternatively on the transducer.

In one embodiment, this 3D image created from ultrasound signals is then used to create a patient-specific intervertebral implant. In one embodiment thereof, this 3D image is then used to create a patient-specific endplate that can be attached to a modular core component of an intervertebral implant.

Figure 1B:
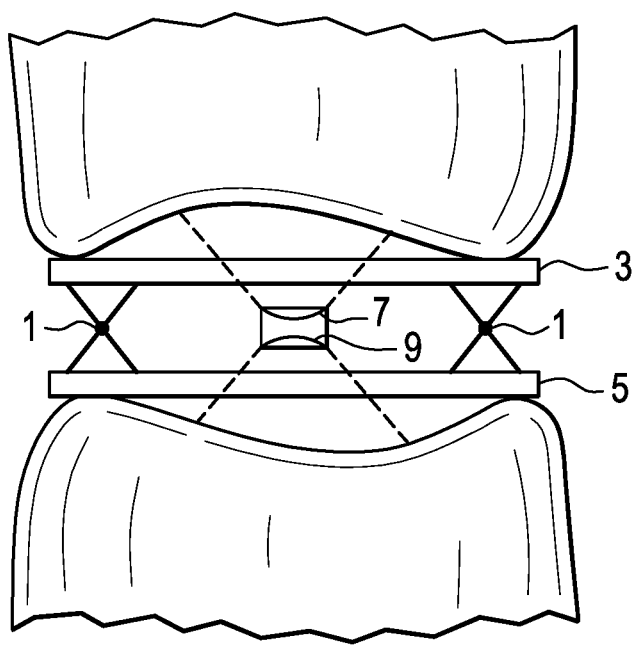

In some embodiments, and now referring to FIGS. 1A and 1B, there is provided a trial comprising:
a) an expandable core component 1 (here shown as a pair of pivoting arms),
b) an upper plate 3 and a lower plate 5, each plate pivotally attached to the core component, and
c) upper 7 and lower 9 cameras located between the core component and the respective plates.

The plates are preferably transparent to light. The core and plate components are first advanced into the disc space and the core is then expanded, so that the plates contact the periphery of the opposed vertebral endplates. Next, the cameras are advanced into the disc space as they emit light (shown as a dotted line) and record images of the upper and lower cavities. These images are then aggregated to produce a 3D image of each cavity.

Figure 3A:
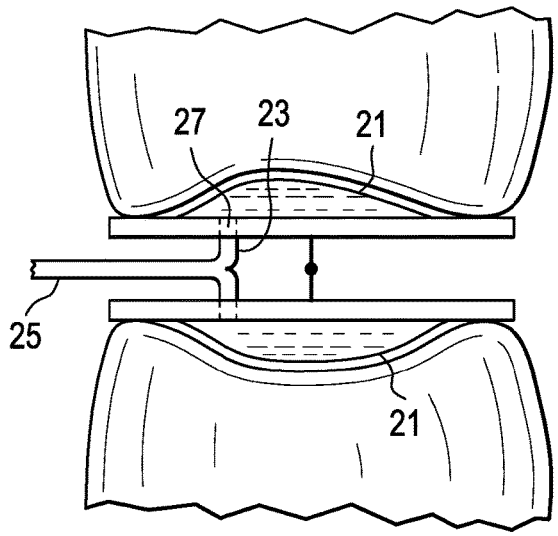
FIGS. 3A-3F disclose embodiments of the balloon molding embodiment of the present invention.
Figure 3B:
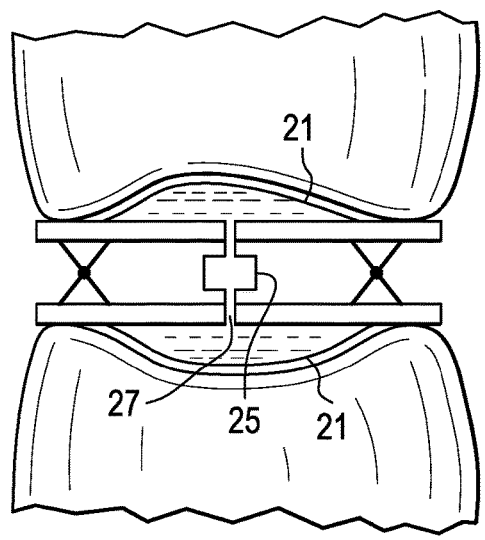
Figure 3D:
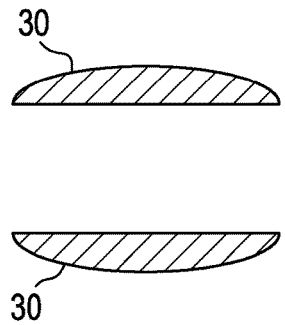
Figure 3E:
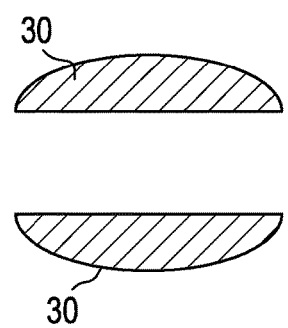
Figure 3F:
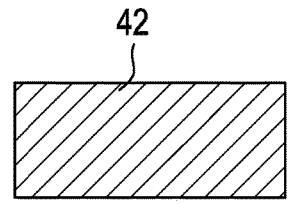
Figure 3C:
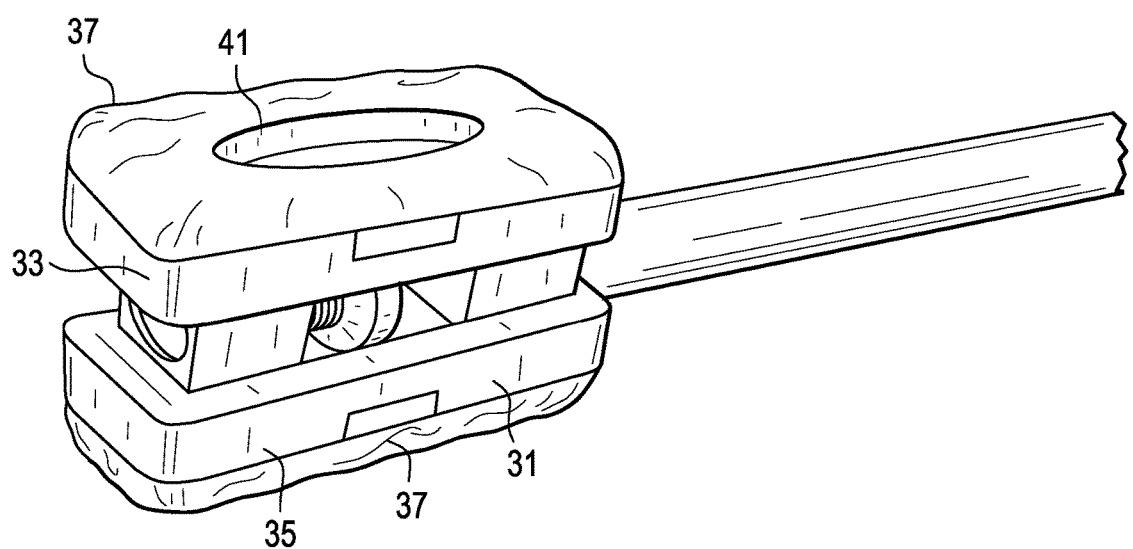

In one embodiment, the 3D images of the cavities between the trial and the opposed vertebral endplates are provided by balloon moldings. In this embodiment, and now referring to FIGS. 3A-3B, an elastic, conformable, deflated balloon is attached to one of the upper and lower surfaces of the trial, and a distal end portion 23 of a tube 25 is connected to the opening of the balloon via a throughhole 27 in the plates. Once the trial is expanded to contact the periphery of the vertebral endplate, a curable fluid is delivered through the tube into the balloon to expand the balloon 21 so that it conforms to the contour of the vertebral endplate. The delivery of the fluid can be halted when a known pressure is obtained. The fluid then cures to a solid resin in the shape of a dome. FIG. 3C shows a perspective view of a balloon-molding trial of the present invention, including the expanding core 31, upper 33 and lower 35 surfaces, and conforming balloons 37. The trial may also have a graft window 41. Next, the expanded trial is retracted so that the cured molding 30 (whose cross sections are shown in FIG. 3D-3E) may be removed from the disc space. In one embodiment, this molding is then used to create a patient-specific intervertebral implant. In one embodiment thereof, this molding is then used to create a patient-specific endplate that can be attached to a modular core component 42 (whose cross-section is shown in FIG. 3F) of an intervertebral implant. In another, this molding is then used to create an entire patient-specific implant. In another, this molding is then used as a template to a machine-finished implant.

In one embodiment, the image feature is adapted from the Lantos AURA™ technology. This technology is described in US2013-0002426; U.S. Pat. No. 8,384,916; US2014-0002613; and U.S. Pat. No. 8,619,154, the specifications of which are hereby incorporated by reference in their entireties. In this embodiment, an elastic, deflated balloon is attached to one of the upper and lower surfaces of the trial, and a distal end of a tube is connected to the opening of the balloon. Once the trial is expanded to contact the periphery of the vertebral endplate, a fluid is delivered into the balloon to expand the balloon so that it conforms to the contour of the vertebral endplate. The delivery of the fluid is halted when a known pressure is obtained. The trial has two light emitters that emit two different wavelength bands of fluorescent light. The trial also has light receivers that register the absorption of the two different lights as they travel through an absorbing medium contained within the balloon. Related imaging technology then captures the images and uses algorithms to combine the images into a full 3D scan of the cavity. This embodiment may also be adapted to use the graduated balloon technology discussed above.

In one embodiment, this 3D image created from these light signals is then used to create a patient-specific intervertebral implant. In one embodiment thereof, this 3D image is then used to create a patient-specific endplate that can be attached to a modular core component of an intervertebral implant.

In some embodiments, the core, plate and balloon components are first advanced into the disc space and the core is then expanded, so that the plates contact the periphery of the opposed vertebral endplates. Next, the elastic balloons are inflated to conform to the contour of the opposed endplates. Next, the cameras are advanced into the disc space (or retracted from the disc space) as they emit light and record images of the balloons as they conform to the upper and lower cavities. The known distance and spacing of the markings on the graduated balloons allow for imaging and determination of the expanded 3D geometry.

Figure 2A:
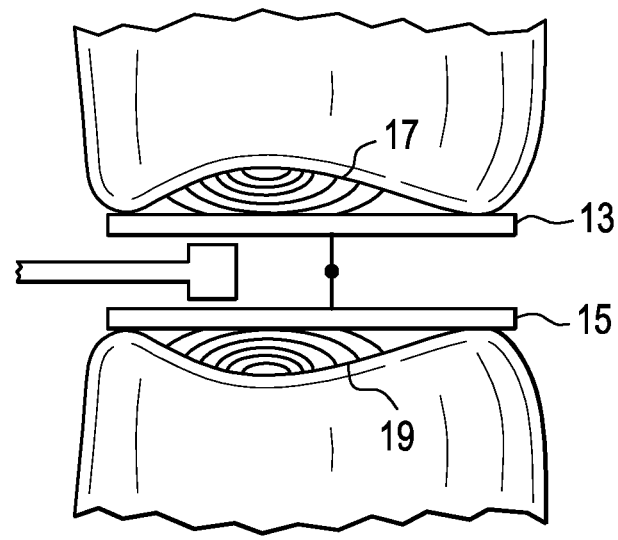
FIG. 2A-2B disclose front and side views of a light imaging embodiment of the present invention using graduated balloons.
Figure 2B:
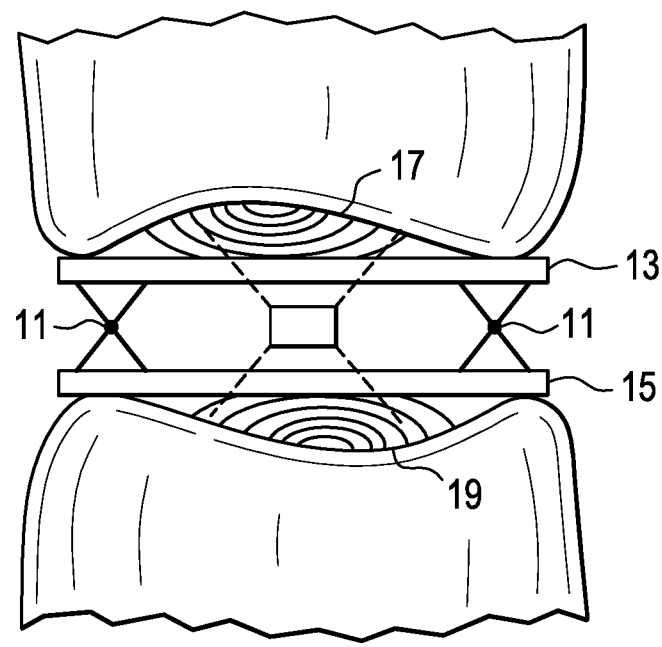

In some embodiments, and now referring to FIGS. 2A and 2B, there is provided a trial comprising:
a) an expandable core component 11 (here shown as a pair of pivoting arms),
b) an upper plate 13 and a lower plate 15, each plate pivotally attached to the core component, and
c) upper 17 and lower 19 graduated balloons attached to the respective plates.

Modular endplates can be milled or machined from blank stock in the operating room based upon information of the 3D geometry of the cavity using known, computer-based rapid prototyping techniques, such as SLA, fusion deposition modeling, selective metal sintering and selective laser sintering. The geometry can be obtained directly from the 3D imaging, directly from the moldings, or by reconstructing of the 3D images obtained from the two or more balloons. This geometry information can be transferred to a milling machine in the form of milling instructions. The endplates can also be 3D-printed by, for example, stereolithography in the operating room. The endplates can also be assembled from modular components which are indicative of typical endplate geometries to create the patient specific devices with enhanced contact area.

Figure 4:
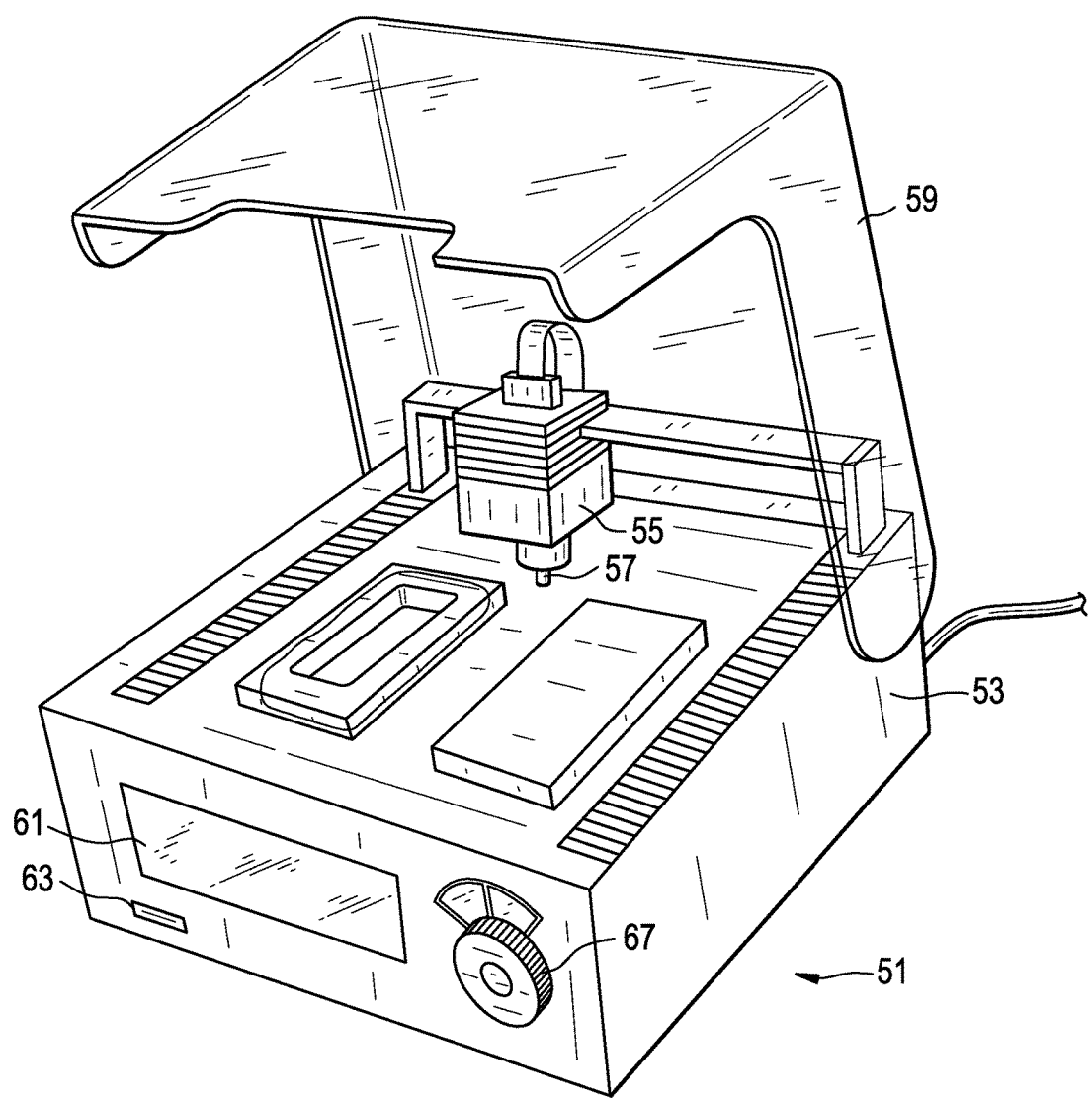
FIG. 4 discloses a perspective view of a milling machine used to make the endplates of the present invention.

In one milling manufacturing embodiment, and now referring to FIG. 4, there is provided an apparatus 51 suitable for manufacturing implants of the present invention. The apparatus has a base 53, a 3D-moveable forming device 55 having replaceable cutting tips 57, a shield 59, a readout 61, an input 63 for receiving milling instructions, a built in bluetooth connection (not shown), and a multifunction knob interface 67. The cutting tips work upon a blank to yield a finished endplate cut to match a patient's specific anatomy.

Figure 5A:
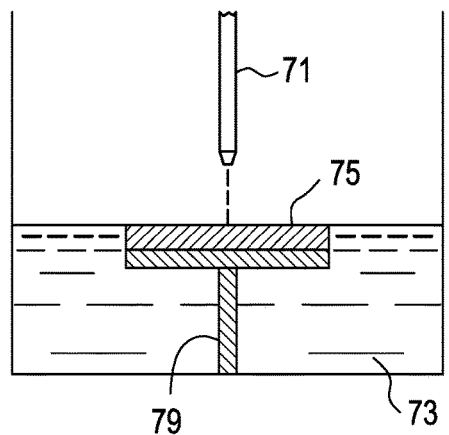
FIGS. 5A-5G disclose a rapid prototyping-based embodiment of the present invention.
Figure 5E:
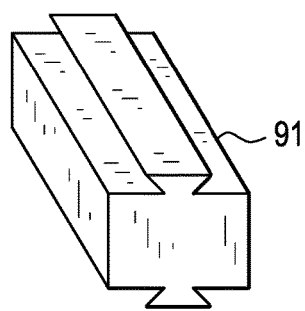
Figure 5F:
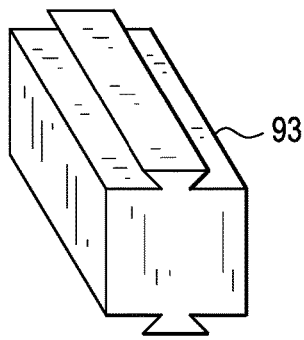
Figure 5G:
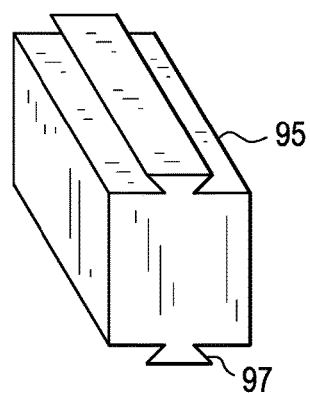
Figure 5B:
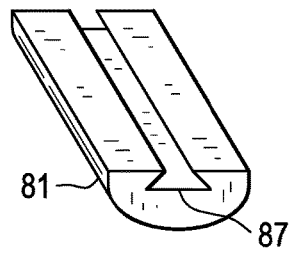
Figure 5C:
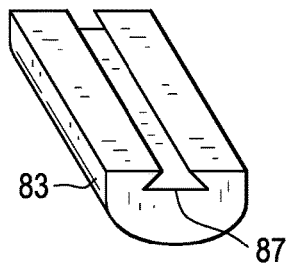
Figure 5D:
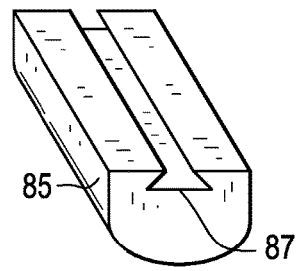

In one stereolithography manufacturing embodiment, and now referring to FIG. 5A, a 3D printer has a light emitter 71 situated above a pool 73 of curable resin. The 3D printer receives printing instructions suitable for producing an endplate of the present invention. In accordance with those instructions, the light emitter emits a beam of light onto the pool surface in a pattern indicative of the endplate to be manufactured. The light causes a chemical reaction to occur in the upper layer of the pool so as to cure that layer and thereby build a layer 75 of the endplate. By retracting scaffold 79, the cured endplate layer is then submerged to expose a new layer of uncured resin at the top of the pool. The process then repeats itself to produce a second cured layer of the endplate, and so on until the entire endplate is produced. The paired endplates so produced, shown in FIGS. 5B-5D, can be provided in small dome 81 (FIG. 5B), medium dome 83 (FIG. 5C) and large dome 85 (FIG. 5D) varieties. These endplates may further be fabricated with dovetail grooves 87, for easy assembly to cores that may be furnished in small 91 (FIG. 5E, medium 93 (FIG. 5F) and large 95 (FIG. 5G) sizes. These cores have matching dovetails 97.

Once the endplates are assembled to the modular core, or once the full device is fabricated, they or it may be inserted into a disc space by any known means. In some instances, to avoid impaction of a cage with the endplate dome which is frequently larger than the disc space entry point, the components of the implant may be serially inserted into the space, whereby the upper and lower endplates are first inserted into the disc space, and then the central core spacer is inserted therebetween to obtain the final implant.

We claim:

1. An intervertebral trial having a distal end portion having upper and lower surfaces defining a height therebetween, wherein the height is adjustable and is adapted for insertion into a disc space between opposing vertebral endplates, and wherein the distal end portion has an imaging feature adapted to map a contour of a vertebral endplate,
    wherein at least one of the upper and lower surfaces has a balloon attached thereto,
    wherein the imaging feature comprises at least one light emitter and a camera, and
    wherein the imaging feature is adapted to carry out light absorption imaging of the balloon.

2. The trial of claim 1 wherein the balloon is filled with a fluid.

3. The trial of claim 1 further having a proximal end portion comprising a handle.

4. The trial of claim 1 further having an elongated intermediate portion.

5. The trial of claim 4 wherein the elongated intermediate portion comprises a rod.

6. The trial of claim 1 wherein the upper and lower surfaces are substantially planar.

* * * * *